United States Patent [19]

Pernet et al.

[11] 4,188,331
[45] Feb. 12, 1980

[54] PROSTAGLANDIN DERIVATIVES

[75] Inventors: André G. Pernet, Kirkland, Canada; Hiromasa Nakamoto, Awara; Naoyasu Ishizuka, Ou, both of Japan

[73] Assignee: Abbott Laboratories, North Chicago, Ill.

[21] Appl. No.: 899,905

[22] Filed: Apr. 26, 1978

Related U.S. Application Data

[60] Continuation-in-part of Ser. No. 746,022, Nov. 30, 1976, abandoned, which is a division of Ser. No. 647,822, Jan. 9, 1976, abandoned.

[51] Int. Cl.$^2$ ............................................. C07D 307/32
[52] U.S. Cl. ................................. 260/343.6; 542/429; 424/279
[58] Field of Search ....................... 260/343.6; 542/429

[56] References Cited

U.S. PATENT DOCUMENTS

| | | | |
|---|---|---|---|
| 3,873,607 | 3/1975 | Bernady et al. | 560/121 |
| 3,883,659 | 5/1975 | Vlattas | 424/285 |

FOREIGN PATENT DOCUMENTS

| | | | |
|---|---|---|---|
| 49-132066 | 12/1974 | Japan | 260/343.6 |
| 1400842 | 7/1975 | United Kingdom | 260/343.6 |

*Primary Examiner*—Alan L. Rotman
*Assistant Examiner*—Natalia Harkaway
*Attorney, Agent, or Firm*—Paul D. Burgauer; Robert L. Niblack

[57] ABSTRACT

Prostaglandin type compounds of the formula

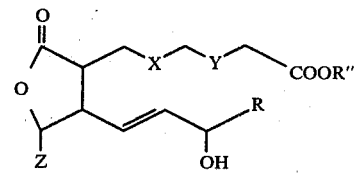

where X is $CH_2\text{—}CH_2$, $CH\text{=}CH$ or $C\text{≡}C$; Y is $CH_2$ or O; Z is OH, $CH_3$ or $CH_2OH$, R" is H or loweralkyl and R is a linear, branched or cyclic alkyl group of 3 to 7 carbon atoms, can be prepared by essentially a one-step reaction from a new intermediate of the formula

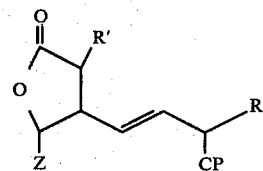

wherein R' is hydrogen, R and Z are the same as shown above, and P is a removable protective group. The new compounds are useful as antihypertensives, gastric acid secretion inhibitors and smooth muscle stimulants.

5 Claims, No Drawings

PROSTAGLANDIN DERIVATIVES

BACKGROUND OF THE INVENTION

This is a continuation-in-part of U.S. Ser. No. 746,022 filed on Nov. 30, 1976 which is a divisional of U.S. Ser. No. 647,822 filed on Jan. 9, 1976, both now abandoned.

BACKGROUND OF THE INVENTION

1. Field of the Invention

This invention relates to novel prostaglandin derivatives, and more particularly novel prostaglandin E derivatives having useful physiological properties and the method of making these novel derivatives.

2. Description of the Prior Art

The prostaglandins comprise one of the most unique and remarkable groups of chemical compounds to emerge in recent years. Extensive research with these agents, conducted largely during the last decade, has provided new insights in the fundamental biological processes and has offered a promise of new potent therapeutic agents.

Chemically, prostaglandins are fatty acids of usually about 20 carbon atoms which contain a 5-membered ring, having 2 attached aliphatic side chains, one carrying a carboxylic acid group at the terminus.

The basic structure, prostanoic acid, is shown as I.

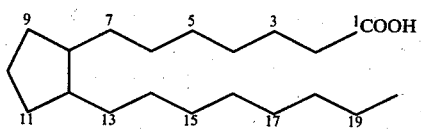

Chemical variations, involving hydroxyl, carbonyl, and structural variances such as unsaturated groups form the various prostaglandins. An abbreviation system for naming these agents is widely used. Following the letters of PG (prostaglandin), the designation of A, B, E, and F is used to denote the specific ring structure. For example, prostaglandin $E_1$ ($PGE_1$) has the following structure:

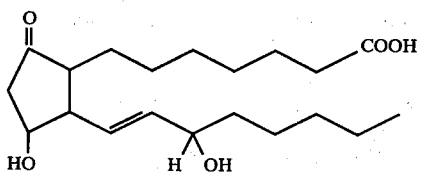

Prostaglandin $E_2$ ($PGE_2$) has the following structure:

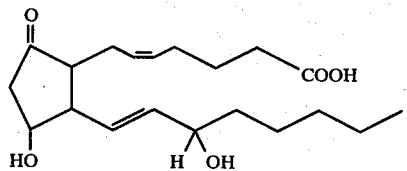

For a discussion of the stereochemistry of the prostaglandins, reference is made to Nature, vol. 212, page 38 (1966).

The prostaglandins are synthesized in the body from poly-unsaturated fatty acids by the formation of a 5-membered ring (cyclopentane ring) and incorporation of three oxygen atoms at certain positions. One of the common fatty acid precursors who are natural prostaglandins is arachidonic acid, the precursor of prostaglandin $E_2$. The main source of arachidonic acid is the phospholipids, which are found in the cell membrane.

The $PGE_2$ compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. $PGE_2$ is also useful as an hypotensive agent to reduce blood pressure in mammals, including man. $PGE_2$ also increases the flow of blood in the mammalian kidney, thereby increasing volume and electrolyte content of the urine. Therefore, the compound is useful in managing cases of renal dysfunction, especially those involving blockage of the renal vascular bed.

DETAILED DESCRIPTION OF THE INVENTION

The new compounds of this invention are used to produce new prostaglandins related to the PGE series which, in turn, are potent vasodilators, gastric secretion inhibitors and smooth muscle stimulants similar to PGE, and $PGE_2$. The naturally occurring prostaglandin E's are subject to rapid metabolic change and therefore have a very short half-life in the body. The novel derivatives described herein have useful pharmacological properties similar to PGEs, but have a much longer half-life in the body because of their increased resistance to metabolic change.

The compounds of the present invention have the formula

IV wherein R' is $CH_2XCH_2YCH_2COOR''$; X is $CH_2-CH_2$, $CH=CH$ or $C\equiv C$; Y is $CH_2$ or O; Z is OH, $CH_3$, $CH_2OH$; R is a linear, branched or cyclic alkyl group of 3 to 7 carbons, R'' is H or loweralkyl, and P is hydrogen or a protective group that can be removed without affecting the rest of the molecule.

It has been found that PGs of various α-chains can be made through a new synthetic route (FIG. 1) involving the above substituted intermediate of formula IV (R'=H). This addition essentially involves only a one-step reaction from the intermediate of formula IV where R'=H and where R, P and Z are defined above.

The preparation of the modified new PGs involve the 1, 4-addition of a cuprate reagent (containing the entire ω-chain) to the compound of the formula

V which is followed by the described introduction of the entire α-chain according to FIG. 1.

The compounds of the formula

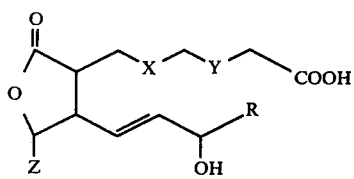

wherein R, X, Y and Z have the above meaning and their ester, except that P=H, possess interesting pharmacological properties when tested in standard pharmacological tests. In particular, they have been found to possess hypotensive, antihypertensive and gastric acid secretion inhibiting properties which make them useful in the treatment of conditions associated with high blood pressure and in the treatment of pathological conditions associated with excessive secretion of gastric acid such as, for example, peptic ulcer.

FIG. 1

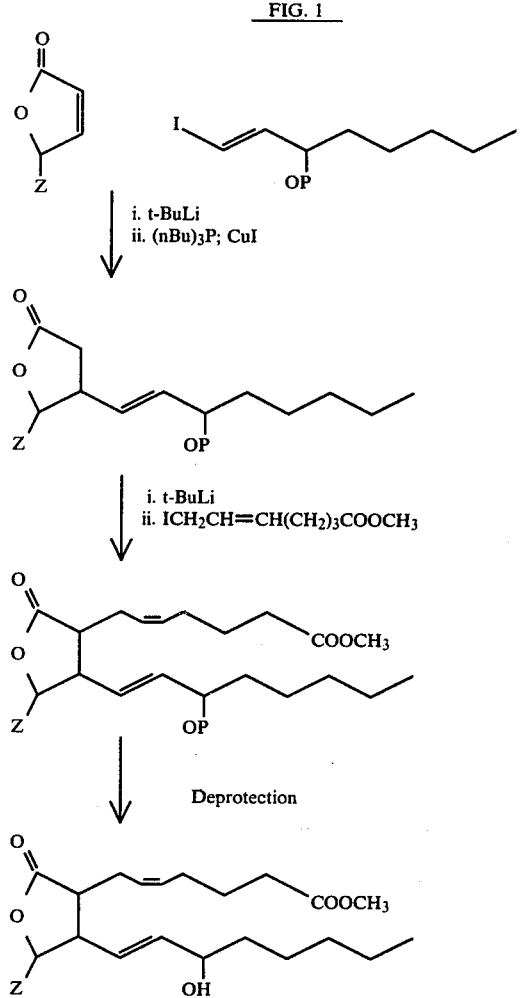

where P is a protective group such as t-butyldimethylsilyl tetrahydropyranyl, or equivalents thereof selected from the protective groups described by MCOMIE, Advances in Organic Chemistry, Methods and Results, Vol. 3, page 216–51 and the Table of page 273 (1963).

FIG. 2

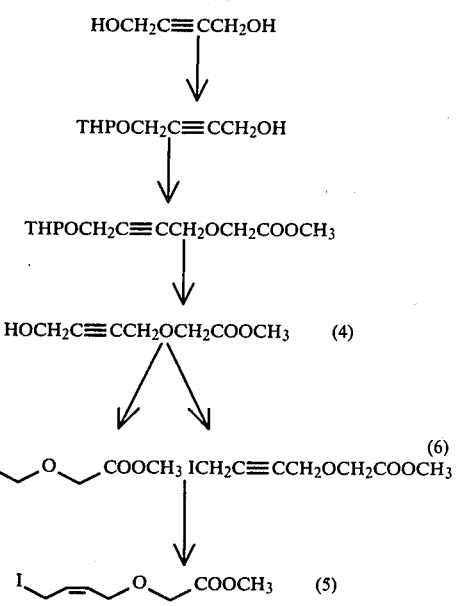

When the compounds of this invention are employed as hypotensive or anti-hypertensive agents, as agents inhibiting gastric acid secretion in warm-blooded animals, for example, in cats or rats, as agents for the prevention or treatment of thrombosis, or as bronchospasmolytic agents, alone or in combination with pharmaceutically acceptable carriers, their proportions are determined by their solubilities, by the chosen route of administration, and by standard medicinal practice. The compounds of this invention may be administered orally in solid form containing such excipients as starch, lactose, sucrose, certain types of clay, and flavoring and coating agents. However, they are preferably administered parenterally in the form of sterile solutions thereof which may also contain other solutes, for example, sufficient sodium chloride or glucose to make the solution isotonic. For use as broncho-spasmolytic agents, the compounds of this invention are preferably administered as aerosols.

The dosage of the present hypotensive, anti-hypertensive, gastric acid secretion inhibiting, or bronchospasmolytic agents, or agents for the prevention and treatment of thrombosis will vary with the forms of administration and the particular hosts under treatment. Generally, treatments are initiated with small dosages substantially less than the optimum doses of the compounds. Thereafter, the dosages are increased by small increments until the optimum effects under the circumstances are reached. In general, the compounds of this invention are most desirably administered at a concentration level that will generally afford effective results without causing any harmful or deleterious side effects and preferably at a level that is in a range of from about −10 μg/kg, although as aforementioned variations will occur. However, a dosage level that is in range of from about 0.5 mg to about 5 mg per kilo is most desirably employed in order to achieve effective results. When administering the compounds of this invention as aerosols the liquid to be nebulized, for example, water, ethyl alcohol, dichlorotetrafluoroethane and dichlorodifluoromethane, contains preferably from 0.005–0.05 percent of the acid, or a non-toxic alkali metal, ammonium or amine salt thereof, or ester of formula IV.

Practical and presently preferred embodiments of the present invention will be illustrated in the following examples, and reference should be made to FIGS. 1 and 2. However, these examples are not intended to limit the invention in any respect other than as defined in the claims.

EXAMPLE 1

Preparation of 3-(3′-t-butyldimethylsilyloxy-1′-octenyl)-γ-valerolactone (A: R=nC$_5$H$_{11}$; R′=H; Z=CH$_3$)

t-BuLi (20 ml; 0.75 M) was rapidly added to 1-iodo-3-t-butyldimethyl-silyloxy-trans-1-octene) (obtained as described by Corey JACS 94, 7210 (1972)) (2.85 g; 7.5 mmoles) at −78° under argon. The mixture was stirred at that temperature for two hours. Independently, nBu$_3$P (1 ml) was added to a suspension of CuI (715 mg; 3.75 mmoles) in 20 ml of ether. After ten minutes, this clear solution was slowly added to the solution to the above octene. The resulting mixture was stirred for one hour. At that point the solution was a faintly yellow suspension.

β-Angelicalactone (367 mg; 3.75 mmoles) was added dropwise. The solution turned dark brown instantly. Stirring was continued at −78° for thirty minutes, then the flask was placed on a CCl$_4$/dry ice bath and the internal temperature rose slowly to −35°. When the temperature rose from −35° to −15°, the solution gradually lost its color. The mixture was stirred at −15° for thirty minutes and HCl (1N) was added (at −15°). Extraction, washing with NH$_4$Cl solution, and concentration of the ether, afforded a mobile colorless syrup.

The product was separated from the less polar residue by chromatography on silicia gel eluted with petroleum ether (30°-60°). The residue of compound 2 (1.53 g) was pure enough for the subsequent steps.

An aliquot was purified by preparative thin-layer chromatography, hereinafter called tlc (petroleum ether: ether; 4:1), IR 1790 cm$^{-1}$ γ lactone, NMR; 5:55 (2H; m; H$_{13}$; H$_{14}$) 4.30–3.90 (2H; m; H$_{11}$; H$_{15}$).

By replacing the named starting material by the corresponding hexene, heptene, undecene, cyclohexylbutene, cyclobutylpentene, 5-methyloctene, 6-methylheptene (R=nC$_3$H$_7$—; nC$_4$H$_9$—; nC$_8$H$_{17}$—;

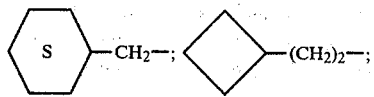

CH$_3$CH$_2$CH$_2$CH(CH$_3$)—CH$_2$—; (CH$_3$)$_2$CH(CH$_2$)$_2$—) etc., other analogs of IV (R′=H) are obtained in the described fashion.

EXAMPLE 2

Preparation of methyl 7-iodo-cis-5-heptenoate

Methyl 7-hydroxy-5-heptynoate (3.9 g) was hydrogenated in the presence of Pd/C 5% (400 mg) and quinoline (1 g) in methanol (50 ml). The mixture was filtered and the methanol concentrated; then the residue was dissolved in dichloromethane and washed twice with water, dried and concentrated to give 3.8 g.

The product (3.8 g; 24 mmoles) was stirred at room temperature for six hours with (PhO)$_3$PCH$_3$I (12.4 g; 27 mmoles) in CH$_2$Cl$_2$/DMF (20 ml, 5 ml). After the organic phase was washed with water, dried and concentrated, the residue was purified on column chromatography and eluted with petroleum ether (30°-60°).

EXAMPLE 3

Preparation of 11-deoxy-11-methyl-10-oxa-prostaglandin E$_2$methyl ester (3; Z=CH$_3$)

nBuli (2.16 ml; 4.32 mmoles) was rapidly added to diisopropylamine (0.65 ml; 4.32 mmoles) in THF (12 ml) at 0°. The mixture was stirred at 0° for one hour, then cooled at −78°. A solution of 2 (1.471 g; 4.32 mmoles) in 2 ml THF was added dropwise. After stirring at −78° for one hour, the iodide of Example 2 (1.16 g; 4.32 mmoles) was added. The mixture was placed on a CCl$_4$/dry ice bath. Color changes occurred as the temperature rose above −60°. After stirring one more hour at −30° to −15°, HCl (1N) was added (at −15°). The product was extracted with ether, washed and concentrated to give 1.982 g of colorless residue.

An aliquot (339 mg) was purified by preparative tlc to afford the pure silyl ether (84 mg; 28% overall yield) derivative 3a.

The remaining crude silyl derivative (1.643 g) was treated with Bu$_4$NF (10 ml; 10 mmoles) to afford crude 3 (1.507 g) which was purified by preparative tlc (13 plates) eluted with petroleum ether: ether; (4:1). The product showed two close spots, diastereomers at positions 11 and 15. Overall yield from angelicalactone: 396 mg (29%).

EXAMPLE 4

The methyl ester of Example 3 was hydrolyzed to the free acid, Compound VI (X=CH=CH cis, Y=CH$_2$, Z=CH$_3$, R=n—C$_5$H$_{11}$) using sodium hydroxide (2 eq) in water: THF (1:1).

By using the compounds identified in the last paragraph of Example 1 and proceeding according to Examples 2–4, the corresponding 10-oxa-analogs of PGEs of formula VI are obtained, carrying the R groups named in Example 1 last paragraph.

EXAMPLE 5

Preparation of 5,6-dehydro-11-deoxy-11-methyl-10-oxa-prostaglandin E$_2$

Replacing the iodide of Example 2 by methyl 7-iodo-5-heptynoate (obtained as described by Corey JACS, 95, 8483 (1973)) in the procedure of Example 3, followed by saponification of the methyl ester, yielded compound VI (X=C≡C, Y=CH$_2$, Z=CH$_3$, R=n—C$_5$H$_{11}$) as a colorless syrup similar in physical properties to the product of Example 4.

EXAMPLE 6

Preparation of methyl-O-(4-hydroxy-2-butynyl)-glycolate(5)

To 2-butyn-1,4-diol (300 g; 3.49 moles) in dioxane (800 ml) in the presence of p-TSOH (3 g), was added dihydropyran (294 g; 3.5 moles) during a period of six hours. The medium was stirred overnight at room temperature then neutralized with solid K$_2$CO$_3$. The solvent was removed without filtration and the residue was dissolved in dichloromethane and washed twice with water. The organic phase was dried, concentrated and distilled to afford the mono tetrahydropyranyl derivative (205 g; 34%) b.p. 92°-98°/0.2 mmHg. This derivative (110 g; 0.649 mole) was added all at once to a solution of potassium t-butoxide freshly prepared from potassium (25.3 g; 0.649 mole) in t-BuOH (600 ml). After three minutes, methyl bromoacetate was added (97.35 g; 0.649 mole). The temperature rose spontaneously to 70°. When the exothermic reaction was completed, the mixture was found to be neutral and the solvent was evaporated under vacuum. The residue (140 g; 88%) was found to be homogeneous on tlc (and was not purified at that stage), and was then heated under reflux in methanol (700 ml) containing a small amount of p-TSOH. After thirty minutes, the medium was allowed to cool down and 0.1 ml of pyridine was added; the solvent was evaporated and the residue distilled, giving the intermediate 4 (FIG. 2) (81.4 g; 89%) b.p. 110°-120°/3 mmHg.

It was hydrogenated as in Example 2 to afford an almost quantitative yield of the cis-alkene, which was iodinated as in Example 2 to afford 5 in 85% yield after chromatography. Compound 5 was found to be unstable and was stored cold under argon. (FIG. 2).

EXAMPLE 7

Preparation of
11-deoxy-3,10-dioxa-11-methyl-prostaglandin $E_2$

The title compound IV (R'=$CH_2$—X—$CH_2$—Y—$CH_2$—COOH; X=—CH=CH— cis; Y=O; Z=$CH_3$; R=n—$C_5$—$H_{11}$) was prepared by using the iodide 5 (FIG. 2) in the procedures of Examples 3 and 4.

EXAMPLE 8

Preparation of methyl
0-[1-(4-iode-2-butynyl)]-glycolate

Iodination of 4 (FIG. 2) by the procedure described in Example 2 gave the desired iodoalkyne 5 (FIG. 2).

EXAMPLE 9

Preparation of
5,6-dehydro-11-deoxy-3,10-dioxa-11-methyl prostaglandin $E_2$

The title compound IV [R'=$CH_2$—X—$CH_2$—Y—$CH_2$—COOH; X=C≡C; Y=O; Z=$CH_3$; R=$(CH_2)_3CH_3$] was prepared by using the iodide 6 (FIG. 2) in the procedures of Examples 3 and 4.

EXAMPLE 10

The preparation of the analogs of the parent 11-deoxy-10-oxa-11-substituted PGEs, having a different number of carbon atoms on the ω-chain, was performed as in Examples 1, 3 and 4 except that the appropriate 1-iodo-4-alkenes were used (total chain lengths 6, 7, 9 and 10).

EXAMPLE 11

Preparation of 3-t-butyldimethylsilyloxy-4-(3'-t-butyldimethylsilyloxy-1'-octenyl)-γ-valerolactone Replacement of β-angelicalactone with 5-hydroxy-2-penten-4-olide [obtained as described by Front [Soc. Espan. Fis. Quim. 62. 477 (1966)] in the procedure of Example 1 and protecting its hydroxy group with t-butyldimethylsilyl yielded intermediate 2 (Z=$CH_2OP$).

Replacement of 2 (FIG. 1) by the above lactone in the procedures of Examples 3 and 4 yielded modified prostaglandins VI wherein Z=$CH_2OH$, the other variations being unaffected.

While the above examples are directed to the use of the t-butyldimethylsilyl group for protection of the otherwise reactive hydroxy groups, almost identical results are obtained by using the more commonly used protective ability of the tetrahydropyranyl group. Any number of other protective groups can be used, as is well recognized by those skilled in the art, each group having its own characteristics and reactivity for insertion in the molecule or the removal from the final PG analog made by use of the current intermediates.

The above examples are primarily directed to compounds that contain a double- or triple bond in the α-chain. It is obvious to those skilled in the art that the corresponding saturated analogs can be made in the same fashion but using a saturated iodide analog in the reaction depicted in FIG. 2(5).

In the foregoing description, substituent P has been used as a protective group which is known to those skilled in the art as being a labile group. It is well known that such groups can easily be removed by mild chemical treatments often requiring no more than placing the protected compound in an otherwise inert acid or base. As shown in the examples, an excellent means for this purpose is tetrabutylammonium fluoride.

The condensation reaction with the α-chain iodide can be carried out in a variety of solvents, but is preferably performed at temperatures well below 0° C. One of the most suitable solvents allowing such a low temperature reaction is tetrahydrafuran but other ethers and alkanes, liquid at temperatures from far below 0° C. to room temperature are equally suitable.

What is claimed is:

1. A compound of the formula

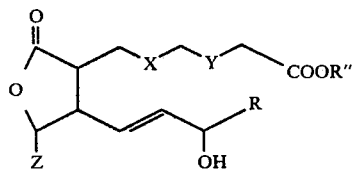

wherein R is a linear, branched or cyclic alkyl group of 3 to 7 carbon atoms; Z is OH or $CH_2OH$, X is —CH=CH— or —C≡C—; Y is O or $CH_2$ and R" is H or loweralkyl.

2. A compound according to claim 1

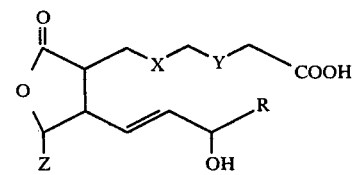

wherein X is —CH=CH— or —C≡C—; Y is $CH_2$ or O; Z is OH or $CH_2OH$ and R is a linear, branched or cyclic alkyl group of 3 to 7 carbon atoms.

3. A compound of the formula

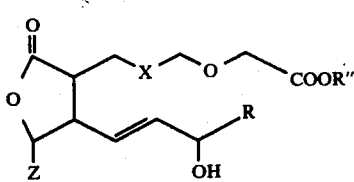
wherein R is a linear, branched or cyclic alkyl group of 3 to 7 carbon atoms; Z is OH, CH₃ or CH₂OH; X is —CH=CH— or —C≡C—; and R" is H or loweralkyl.
4. The compound according to claim 3 where X is —CH=CH—; Y is O, Z is CH₃ and R is n—C₅H₁₁.
5. The compound according to claim 3 where X is —C≡C—; Y is O, Z is CH₃ and R is n—C₄H₉.
* * * * *